United States Patent [19]

Yorozu et al.

[11] Patent Number: 5,389,678
[45] Date of Patent: Feb. 14, 1995

[54] SOLUBLE ALUMINUM CARBOXYLATE BATHING PREPARATION

[75] Inventors: Hidenori Yorozu; Hirotaka Sato, both of Utsunomiya; Yasuhiro Doi, Ichikaimachi, all of Japan

[73] Assignee: Kao Corporation, Tokyo, Japan

[21] Appl. No.: 108,302

[22] Filed: Aug. 19, 1993

Related U.S. Application Data

[62] Division of Ser. No. 895,006, Jun. 8, 1992, Pat. No. 5,310,758.

[30] Foreign Application Priority Data

Jun. 10, 1991 [JP] Japan ................... 3-137829

[51] Int. Cl.⁶ ............................................. A61K 31/19
[52] U.S. Cl. ..................................... 514/557; 514/558
[58] Field of Search ................. 514/53, 547, 557, 558, 514/552, 835; 424/52, 48, 57

[56] References Cited

U.S. PATENT DOCUMENTS

| | | | |
|---|---|---|---|
| 3,608,086 | 9/1971 | Halpern | 424/317 |
| 4,042,680 | 8/1977 | Muhler et al. | 424/55 |
| 4,108,981 | 8/1978 | Muhler et al. | 424/55 |
| 4,645,662 | 2/1987 | Nakashima et al. | 424/52 |
| 4,885,282 | 12/1989 | Thornfeldt | 514/53 |

*Primary Examiner*—Marianne M. Cintins
*Assistant Examiner*—T. J. Criares
*Attorney, Agent, or Firm*—Oblon, Spivak, McClelland, Maier & Neustadt

[57] ABSTRACT

Bathing preparations comprising a soluble aluminum carboxylate exhibit excellent dissolvability into bath water, and give a refreshing sensation to users during bathing and after bathing.

3 Claims, No Drawings

SOLUBLE ALUMINUM CARBOXYLATE BATHING PREPARATION

This is a division of application Ser. No. 07/895,006, filed on Jun. 8, 1992, now U.S. Pat. No. 5,310,758.

BACKGROUND OF THE INVENTION

1. Field of the Invention

The present invention relates to a bathing preparation, and more particularly to a bathing preparation having an excellent ability of being dissolved (hereinafter referred to as "dissolvability") into bath water, providing an excellent feel to users during bathing and after bathing, and providing excellent bathing effects; a bath containing such a bathing preparation; and a method of bathing using such a bath.

2. Discussion of the Background

Conventionally, various compositions have been known as bathing preparation compositions, and among them, compositions containing so-called hot spring ingredients, which are obtainable from hot spring water, have widely been used. Examples of such hot spring ingredients include sodium chloride, sodium sulfate, magnesium sulfate, sodium hydrogencarbonate and potassium aluminum sulfate (from alum spring).

Among various spring waters, alum spring water contains aluminum ions, which are positive ions, and sulfate ions, which are negative ions, as main ingredients. It is well known that alum spring water provides various bathing effects, such as astringency to the skin and mucous membrane, and treating of chronic skin diseases such as conjunctivitis and inflammation of the mucous membranes, and that the alum spring water is also effective for treating hyperhidrosis of the hands and legs and varicosis.

Accordingly, various attempts have been made to use aluminum sulfate as an ingredient of a bathing preparation.

However, when a large amount of aluminum sulfate is incorporated into a bathing preparation, the following problems arise: The color of bath water cannot be controlled when the bathing preparation is dissolved in the bath water, because of sulfate reduction bacteria existing in the bath water. Further, since aluminum sulfate is sparingly soluble in bath water, it doesn't meet the requirements of complete dissolvability. Moreover, when aluminum sulfate is incorporated into a so-called carbon dioxide bathing preparation, which contains carbonate and acid as main ingredients, the aluminum sulfate coheres in the bath water upon use, thereby producing floating substances on the surface of the bath water.

Therefore, there remains a need for a bathing preparation which has the same bathing effects as those of alum spring, has an excellent dissolvability into bath water, and gives an excellent sensation to users during bathing and after bathing.

SUMMARY OF THE INVENTION

Accordingly, it is an object of the present invention to provide novel bathing preparations which exhibit an excellent dissolvability into bath water, and give a refreshing feel to users during bathing and after bathing through skin sensation.

It is another object of the present invention to provide a bath containing such a bathing preparation.

It is another object of the present invention to provide a method of bathing utilizing such a bath.

These and other objects, which will become apparent during the following detailed description, have been achieved by the inventors' discovery that bathing preparations comprising a soluble aluminum carboxylate exhibit excellent dissolvability in bath water and that bathing in a bath containing such a bathing preparation provides the bather with a refreshing sensation during and after bathing.

DETAILED DESCRIPTION OF THE PREFERRED EMBODIMENTS

Examples of the soluble aluminum carboxylate suitable for use in the present bathing preparation include aluminum monocarboxylates such as aluminum glycolate, aluminum lactate, aluminum glycerate and aluminum gluconate; aluminum dicarboxylates such as aluminum tartrate and aluminum malate; aluminum tricarboxylates such as aluminum citrate. Among them, aluminum hydroxy monocarboxylates such as aluminum lactate are particularly preferred.

These soluble aluminum carboxylates can be used singly or in combination. Although the amount of the soluble aluminum carboxylate incorporated in the bath preparation is not particularly limited, it is preferred that the amount incorporated be so determined that the concentration of soluble aluminum carboxylate in the bath water falls in a range of $6.7 \times 10^{-5}$ to $1.3 \times 10^{-2}$ wt. %, preferably $3.3 \times 10^{-4}$ to $1.0 \times 10^{-2}$ wt. %, based on the total weight of the bath water, when the bathing preparation is dissolved in bath water.

The amount of soluble aluminum carboxylate incorporated into a bathing preparation changes depending on the amount of the bathing preparation which is used at a time. It is preferred that the amount of soluble aluminum carboxylate for 150 liters of bath water be in a range of 0.1-20 g, particularly 0.5-15 g. To use the above-mentioned amount of soluble aluminum carboxylate, soluble aluminum carboxylate is incorporated into a bathing preparation in an amount of 0.1 wt. % or more, particularly 0.5-50 wt. %, based on the total weight of the bathing preparation.

The bathing effects of the present bath preparation can be enhanced by using an acid and a carbonate at the same time. Thus, in a preferred embodiment, the present bath preparation further comprises an acid and a carbonate. Any acid and carbonate which are generally incorporated into bathing preparations can be incorporated into the bathing preparation of this invention. Preferred acids are organic acids such as succinic acid, fumaric acid, malic acid, adipic acid and tartaric acid, and preferred carbonates include sodium carbonate, sodium hydrogencarbonate, magnesium carbonate and potassium carbonate.

One or more acids selected from the above-mentioned acids may be used together with one or more carbonates selected from the above-mentioned carbonates. Although the amounts of acid and carbonate incorporated in the bath preparation are not particularly limited, it is preferred that the incorporation ratio between acid and carbonate be adjusted so that the pH of the bath water falls in the range of 5-7 (0.01 wt. % solution). At such conditions, it is possible to maintain carbon dioxide dissolved in the bath water, thereby providing excellent bathing effects such as improving the circulation of the blood. Even when the incorporation ratio between acid and carbonate is so chosen that the pH of bath water does not fall in the range of 5-7, the bathing preparation can be used as an effervescence bathing preparation.

Further, it is preferred that the acid be incorporated in an amount of 5-80 wt. %, particularly 10-50 wt. %, based on the total weight of the present bathing preparation, and that the carbonate be incorporated in an amount of 5-80 wt. %, particularly 10-50 wt. %, based on the total weight of the present bathing preparation.

The present bathing preparation may further contain optional materials which are generally incorporated into bathing preparations.

Examples of such materials include inorganic salts such as sodium chloride, potassium chloride, sodium sulfate, sodium thiosulfate, borax, sodium sulfide, sodium nitrate, sodium phosphate, sodium polyphosphate, calcium oxide, magnesium oxide and potassium sulfide; inorganic acids such as boric acid, metasilicic acid and silicic anhydride, and salts thereof; crude drugs such as fennel, camomile, cinnamon, safflower, peony root, ginger, Japanese iris, conidium rhizome, Japanese angelica root, citrus unshiu peel, atractylodes lancea rhizome, powdered Japanese valerian, angelica dahurica root, bitter orange peel, mentha herb, hoelen, ginseng; colorants; perfumes and the like.

The bathing preparation of this invention can be prepared by any suitable known method in which soluble aluminum carboxylate is mixed with optional ingredients mentioned above, and acid and carbonate when desired.

Examples of preferred forms of the bath preparation include powders, larger particles, granules and tablets. When acid and carbonate are incorporated into the present bathing preparation, tablets are the preferred form, because they can increase the amount of carbon dioxide dissolved into the bath water. Further, excipients and lubricants may be added for the preparation of tablets.

The bathing preparation according to this invention exhibits excellent dissolvability into bath water, and gives a refreshing feel to bathers during bathing and after bathing through their skin sensation.

In another embodiment, the present invention relates to a bath which contains the present bath preparation. Thus, the present invention relates to a bath comprising water and an aluminum carboxylate, wherein the aluminum carboxylate is present in an amount of $6.7 \times 10^{-5}$ to $1.3 \times 10^{-2}$ wt. %, preferably $3.3 \times 10^{-4}$ to $1.0 \times 10^{-2}$ wt. %, based on the total weight of the bath water, with the balance being water.

In a preferred embodiment, the present bath further comprises an acid and a carbonate both of which are selected from those described above. Preferably, the acid and the carbonate are present in the bath in relative amounts such that the pH of the bath is in the range of 5-7. Preferably, the concentration of acid in the bath is $3.3 \times 10^{-3}$ to $2.7 \times 10^{-2}$ wt. %, most preferably $5.0 \times 10^{-3}$ to $1.7 \times 10^{-2}$ wt. %, based on the total weight of the bath, and the concentration of the carbonate in the bath is $1.7 \times 10^{-3}$ to $2.7 \times 10^{-2}$ wt. %, most preferably $3.3 \times 10^{-3}$ to $1.7 \times 10^{-2}$ wt. % based on the total weight of the bath. Of course, the present bath may further comprise one or more of the above-described optional materials in the conventional amount.

Typically, the present bath will be of sufficient volume for immersion of a part of the body from as small as an extremity, such as a hand or foot, to as large as the whole body, preferably excluding the head. Thus, the bath will suitably have a volume of 1 to 300 liters, preferably 100 to 200 liters.

The present bath may be prepared by dissolving the present bathing preparation in a sufficient amount of water.

In another embodiment, the present invention relates to a method of bathing comprising immersing a part of a human body in the present bath. As noted above, the part of the human to be immersed may be as small as an extremity such as a hand or foot, to as large as the whole body, preferably excluding the head. Suitably, the immersion is carried out for a time of one minute to two hours, preferably 5 minutes to 1 hour. For best results the temperature of the bath should be in the range of 35° to 45° C., preferably about 40° C. at the beginning of the immersion. In the usual procedure utilizing a conventional bath tub without a heat source the bath temperature will gradually decrease during the immersion. However, the present invention may be practiced with a bath tub which is equipped with a heating device so that the preferred temperature of the bath may be maintained throughout the immersion.

Other features of the invention will become apparent in the course of the following descriptions of exemplary embodiments which are given for illustration of the invention and are not intended to be limiting thereof.

EXAMPLES

Example 1

The bathing preparations shown in Table 1 were prepared by a known method to obtain tablets or powders thereof which are to be used in an amount of 50 g at a time. They were evaluated in terms of dissolvability and feel to the skin according to the following evaluation methods.

Evaluation of Dissolvability

Each of the present bathing preparations and comparative bathing preparations was dissolved in an amount of 50 g into 150 liters of bath water (40° C.) to evaluate their dissolvability. The results are shown in Table 1. Comparative bathing preparation No. 3 produced floating substances, and its dissolvability was bad.

TABLE 1

| | (Mixture amount: wt. %) | | | | |
|---|---|---|---|---|---|
| | Present Bathing Preparations | | Comparative Bathing Preparations | | |
| | 1 | 2 | 1 | 2 | 3 |
| Aluminum lactate | 10 | 12 | — | — | — |
| Sodium hydrogen-carbonate | 15 | 20 | 15 | 20 | 15 |
| Sodium carbonate | 15 | — | 15 | — | 15 |
| Dextrin | 12 | 58 | 22 | 70 | 12 |
| Succinic acid | 40 | — | 40 | — | 40 |
| Polyethylene glycol 6000 | 8 | 10 | 8 | 10 | 8 |
| Aluminum sulfate | — | — | — | — | 10 |
| Preparation form | Tablet | Powder | Tablet | Powder | Tablet |
| Dissolvability | Good | Good | Good | Good | Bad |

Evaluation of Feel to the Skin

Each of the present bathing preparations 1 and 2, and the comparative bathing preparations 1, 2 and 3 was dissolved in 20 liters of water (40° C.) in such amount that is equal to the proportion of 50 g of composition per 150 liters bath water. 10 panelists carried out the following evaluation test in a room at 30° C. and 70–90% relative humidity: Each panelist put one of his or her forearms into water, into which the present bathing preparation was dissolved, for 10 minutes, while the other forearm was put into water, into which the comparative bathing preparation was dissolved, for 10 minutes. They evaluated the feel to the skin during the immersion. The feel to the skin thus evaluated represents "feel to the skin during bathing". Further, they took their forearms out from water, and toweled their forearms to evaluate the feel to the skin and refreshing feel. The feel to the skin and the refreshing feel thus evaluated represent "feel to the skin after bathing", and "refreshing feel after bathing", respectively. The results are shown in Table 2, in which the results are shown by the number of panelists.

TABLE 2

| Comparison | Evaluation | Present preparation is better | Did not find difference | Comparative preparation is better |
|---|---|---|---|---|
| Comparison between present preparation 1 and comparative preparation 1 | Feel to the skin during bathing | 7 | 2 | 1 |
| | Feel to the skin after bathing | 6 | 3 | 1 |
| | Refreshing feel after bathing | 8 | 2 | 0 |
| Comparison between present preparation 1 and comparative preparation 3 | Feel to the skin during bathing | 6 | 3 | 1 |
| | Feel to the skin after bathing | 6 | 4 | 0 |
| | Refreshing feel after bathing | 8 | 2 | 0 |
| Comparison between present preparation 2 and comparative preparation 2 | Feel to the skin during bathing | 7 | 2 | 1 |
| | Feel to the skin after bathing | 7 | 2 | 1 |
| | Refreshing feel after bathing | 9 | 0 | 1 |

As is clearly understood from Tables 1 and 2, the bathing preparations according to the present invention exhibited an excellent dissolvability, and gave an excellent feel to users.

Example 2

The bathing preparations shown in Table 3 were prepared by a known method to obtain tablets thereof which are to be used in the amount of 50 g at a time, and samples of each tablet were dissolved into 150 liters of bath water (40° C.) for evaluation. Namely, 5 panelists immersed their bodies in the bath water for 5 minutes in a room at 30° C. and 70–90% relative humidity to evaluate the feel to the skin during bathing. Further, after bathing they toweled their bodies and evaluated the feel to the skin after bathing and refreshing feel after bathing. The evaluations were carried out for two successive days. The results of the evaluations were ranked in accordance with the following criteria to obtain evaluation points for each preparation. The results are shown in Table 3 where the average values of the evaluation points are given.

5: Good
4: Slightly good
3: So-so
2: Slightly bad
1: Bad

TABLE 3

| | (Mixture amount: wt. %) | |
|---|---|---|
| | Present Bathing Preparation 3 | Comparative Bathing Preparation 4 |
| Aluminum citrate | 15 | — |
| Sodium hydrogencarbonate | 15 | 15 |
| Sodium carbonate | 15 | 15 |
| Dextrin | 10 | 25 |
| Succinic acid | 30 | 30 |
| Fumaric acid | 10 | 10 |
| Polyethylene glycol 6000 | 5 | 5 |
| Preparation form | Tablet | Tablet |
| Feel to the skin during bathing | 3.8 (5, 4, 4, 3, 3) | 2.8 (3, 3, 3, 3, 2) |
| Feel to the skin after bathing | 4.2 (5, 5, 4, 4, 3) | 2.6 (3, 3, 3, 2, 2) |
| Refreshing feel after bathing | 4.6 (5, 5, 5, 4, 4) | 2.2 (3, 3, 2, 2, 1) |

As is clearly understood from Table 3, the bathing preparation according to the present invention gave excellent feel to users.

Obviously, numerous modifications and variations of the present invention are possible in light of the above teachings. It is therefore to be understood that, within the scope of the appended claims, the invention may be practiced otherwise than as specifically described herein.

What is claimed is:

1. A method of bathing a human individual to impart a refreshing feeling to the individual, comprising immersing a part of the body of the individual, excluding the head, in a bath comprising soluble aluminum carboxylate and water, wherein said soluble aluminum carboxylate is present in an amount of $6.7 \times 10^{-5}$ to $1.3 \times 10^{-2}$ wt. % based on the total weight of said bath and the aluminum salt incorporated into said bath is solely said soluble aluminum carboxylate.

2. The method of claim 1, wherein said soluble aluminum carboxylate is selected from the group consisting of aluminum glycolate, aluminum lactate, aluminum glycerate, aluminum gluconate, aluminum tartrate, aluminum malate, aluminum citrate, and mixtures thereof.

3. The method of claim 1, wherein said soluble aluminum carboxylate is an aluminum hydroxy monocarboxylate.

* * * * *